United States Patent
Szramka et al.

(10) Patent No.: US 9,845,328 B2
(45) Date of Patent: Dec. 19, 2017

(54) METHOD FOR MANUFACTURING OF VARDENAFIL AND ITS SALTS

(71) Applicant: Zaklady Farmaceutyczne Polpharma S.A., Starogard Gdanski (PL)

(72) Inventors: Roman Szramka, Gniew (PL); Jerzy Drygas, Krotoszyn (PL); Marcin Szulc, Starogard Gdanski (PL); Robert Rynkiewicz, Starogard Gdanski (PL)

(73) Assignee: ZAKLADY FARMACEUTYCZNE POLPHARMA S.A., Starogard Gdanski (PL)

( * ) Notice: Subject to any disclaimer, the term of this patent is extended or adjusted under 35 U.S.C. 154(b) by 0 days.

(21) Appl. No.: 15/104,285

(22) PCT Filed: Dec. 8, 2014

(86) PCT No.: PCT/PL2014/000135
§ 371 (c)(1),
(2) Date: Jun. 14, 2016

(87) PCT Pub. No.: WO2015/093994
PCT Pub. Date: Jun. 25, 2015

(65) Prior Publication Data
US 2016/0311827 A1    Oct. 27, 2016

(30) Foreign Application Priority Data
Dec. 16, 2013  (PL) .......................... 406524

(51) Int. Cl.
*C07D 487/04* (2006.01)
*C07D 403/10* (2006.01)

(52) U.S. Cl.
CPC ......... *C07D 487/04* (2013.01); *C07D 403/10* (2013.01)

(58) Field of Classification Search
CPC ........................... C07D 487/04; C07D 403/10
USPC ......................................................... 544/184
See application file for complete search history.

(56) References Cited

U.S. PATENT DOCUMENTS

| | | | |
|---|---|---|---|
| 6,362,178 B1* | 3/2002 | Niewohner | C07F 9/6561 514/218 |
| 6,777,551 B2* | 8/2004 | Nowakowski | C07D 487/04 544/112 |
| 7,977,478 B2* | 7/2011 | Sajja | C07D 487/04 544/184 |
| 2007/0197535 A1* | 8/2007 | Sajja | C07D 487/04 514/243 |

FOREIGN PATENT DOCUMENTS

| | | |
|---|---|---|
| EP | 1695976 A1 | 8/2006 |
| WO | 9924433 | 5/1999 |
| WO | 0250076 A2 | 6/2002 |
| WO | 2004006894 A1 | 1/2004 |
| WO | 2013075680 A1 | 5/2013 |

OTHER PUBLICATIONS

Prasad et al. Applicaion 1877/CHE/2012, p. 1, Filing date May 11, 2012, Publication date Nov. 15, 2013.*
Sulphonyl Halides found in Rodd's Chemistry of Carbon Compounds, Second Edition, S. Coffee, ED, London, vol. III, Part A, Published 1971, p. 447.
Vogel's Practical Organic Chemistry; Fifth Edition, Brian S. Furniss Editor, Longman Group, UK Limited, 1989, pp. 877-878.
X-ray Diffraction, 941 from Physical Tests, United States Pharmacopeia-National Formulary (USP25 NF20), pp. 2088-2089.
Esteve et al.; "New Pyrrolopyrimidin-6-yl Benzenesulfonamides: Potent A2B Adenosine Receptor Antagonists"; Bioorganic & Medicinal Chemistry Letters; 16;pp. 3642-3645; (2006).
International Search Report and Written Opinion; International Application No. PCT/PL2014/000135; International Filing Date Dec. 8, 2014; Date of Mailing Feb. 18, 2015; 10 pages.
IN Application 1877/CHE/2012 filed Nov. 5, 2012; applicant Mylan Laboratories LTD for "Improved Process for the Preparation of Vardenafil Hydrochloride"; abstract; 1 page.
IN 1877/CHE/2012 Filed Nov. 5, 2012_Description and Claims_ pp. 2-11.

* cited by examiner

*Primary Examiner* — Venkataraman Balasubramanian
(74) *Attorney, Agent, or Firm* — Cantor Colburn LLP (57) ABSTRACT

The method of synthesizing vardenafil base, in anhydrous conditions, by chlorosulfonation of 2-(2-etoxy-phenyl)-5-methyl-7-propyl-iH-imidazo[5,1-fJ[1,2,4]triazin-4-one in a mixture of thionyl chloride and sulfurochloridic acid followed by amidation of the product, 4-etoxy-3-(5-methyl-4-oxo-7-propyl-3,4-dihydroimidazo[5,1-f][1,2,4]triazin-2-yl) benzene-sulfonic acid chloride with N-ethylpiperazine, in an aprotic solvent, in the presence of an inorganic base and the method of conversion the product, vardenafil base, to yield vardenafil monohydrochloride trihydrate having a melting point of 234° C. by contacting with water of the anhydrous modification V of vardenafil monohydrochloride in an organic solvent. The subject of the invention is also the anhydrous modification V of vardenafil monohydrochloride and its use in the preparation of vardenafil monohydrochloride trihydrate having a melting point of 234° C.

16 Claims, 5 Drawing Sheets

METHOD FOR MANUFACTURING OF VARDENAFIL AND ITS SALTS

CROSS REFERENCE TO RELATED APPLICATIONS

This application is a National Stage application of PCT/PL2014/000135, filed Dec. 8, 2014, which claims the benefit of Polish Application No. P.406524, filed Dec. 16, 2013, both of which are incorporated by reference in their entirety herein.

The subject of the invention is the method for preparation of vardenafil and its monohydrochloride trihydrate, a medicine used for treating erectile dysfunction.

Vardenafil (2-[2-ethoxy-5-(4-ethylpiperazine-1-sulfonyl)-phenyl]-5-methyl-7-propyl-3H-imidazo[5,1-f][1,2,4]triazin-4-one) is a known strong inhibitor of the phosphodiesterase acting on 3',5'-guanosine cyclic monophosphate (cGMP-PDE) and is used in health care, especially in treating erectile dysfunction.

Vardenafil and the method of its synthesizing was described in patent application WO99/24433. The application discloses a method of synthesizing vardenafil comprising the chlorosulfonation of imidazotriazinone (2-(2-ethoxyphenyl)-5-methyl-7-propyl-3H-imidazo[5,1-f][1,2,4]triazin-4-one) with excess sulfurochloridic acid, and then the decomposition of the unreacted acid with a mixture of ice and water. The product of the reaction, imidazotriazinone sulfochloride (4-ethoxy-3-(5-methyl-4-oxo-7-propyl-3,4-dihydroimidazo[5,1-f][1,2,4]triazin-2-yl)benzene-sulfonic acid chloride) is separated in solid form with a 91% yield. In the next step the imidazotriazinone sulfochloride is amidated with N-ethylpiperazine in methylene chloride. Vardenafil base (2-[2-ethoxy-5-(4-ethylpiperazine-1-sulfonyl)-phenyl]-5-methyl-7-propyl-3H-imidazo[5,1-f][1,2,4]triazin-4-one) is synthesized with a 66% yield.

In patent application WO2002/50076 the authors report that imidazotriazinone sulfochloride is an intermediate which is susceptible to hydrolysis and suggest a different synthesis route for vardenafil, where during the synthesis of imidazotriazinone sulfochloride and its later amidation no water is used. The method is based on the sulfonation of imidazotriazinone with excess concentrated sulfuric acid. The resulting imidazotriazinone sulfonic acid (4-ethoxy-3-(5-methyl-4-oxo-7-propyl-3,4-dihydroimidazo[5,1-f][1,2,4]triazin-2-yl)benzene-sulfonic acid) is separated from the reaction mixture by water crystallization with a ca. 80% yield. In the next step the dried imidazotriazinone sulfonic acid is chlorinated with thionyl chloride in the presence of catalytic amount of dimethylformamide to give imidazotriazinone sulfochloride. The excess thionyl chloride is removed by distillation and the resulting mixture is amidated with N-ethylpiperazine to vardenafil base. The total yield of the chlorination and amidation processes is ca. 93%.

A reference drug Levitra® of Bayer Pharma contains vardenafil as a hydrated salt, i.e. monohydrochloride trihydrate so, from a commercial point of view, the method for synthesis of the said monohydrochloride hydrate is of special importance.

In patent application WO99/24433, besides vardenafil base, its salts and hydrates are presented. In particular, vardenafil monohydrochloride, vardenafil dihydrochloride and vardenafil monohydrochloride trihydrate were disclosed.

Patent application WO99/24433 discloses a general method for preparation of vardenafil monohydrochloride trihydrate by crystallization of vardenafil base from a mixture of organic solvent and aqueous hydrochloric acid and reported that the melting point of that compound is 218° C.

The authors of patent application WO2004/006894 report that vardenafil hydrochloride appears in four different polymorphic forms which they call anhydrous modifications and have the following melting points: I with a melting point of 217° C., modification II with a melting point of 190° C., modification III with a melting point of 183-186° C. and modification IV with a phase transition temperature of 166° C. Furthermore a method for preparation of vardenafil monohydrochloride trihydrate is disclosed, during drug formulation process, by contacting of formulating process mixtures or ready tablets containing any mixture of the above-mentioned anhydrous modifications and optionally vardenafil monohydrochloride trihydrate with a wet gas. In patent application WO2002/50076 was disclosed a method of preparation of crystalline vardenafil monohydrochloride trihydrate in a reaction of concentrated hydrochloric acid with vardenafil base in an acetone/water mixture at a volume ratio of 12:1, and later its crystallization by cooling and seeding of the solution. The obtained vardenafil monohydrochloride trihydrate had a melting point of 192° C.

Several methods for the synthesis of vardenafil monohydrochloride trihydrate are described in patent application, WO2013/075680:
a method based on precipitation in water by a change of pH of an aqueous solution of vardenafil dihydrochloride,
a method based on precipitation in water by a change of pH of an aqueous solution of vardenafil sodium salt,
a method based on recrystallization from water,
a method based on recrystallization from acetone/water solution (10:1),
a method based on crystallization from acetone/water solution (15:1) from vardenafil base and concentrated hydrochloric acid.

Vardenafil monohydrochloride trihydrates prepared in any of those ways were characterized by identical powder diffractograms according to patent application WO2004/006894 (FIG. 8, Tab. 8) and their melting points were in the range 193-198° C.

The essence of the present invention is the method for synthesis of vardenafil base under anhydrous conditions which eliminate the risk of formation of the unwanted imidazotriazinone sulfonic acid and improving purity and yield of the final product.

In a method of the present invention, vardenafil base is synthesized in two chemical reactions, while water is not introduced until the last reaction ends and substances that remove any traces of water are added.

In the embodiment of the invention, the first reaction is the chlorosulfonation of imidazotriazinone with sulfurochloridic acid in a chlorinating solvent, i.e. thionyl chloride. In contrary to the methods known in the prior art for the chlorosulfonation of imidazotriazinone with sulfurochloridic acid in low temperatures, a preferred embodiment of the invention is to perform the reaction under reflux at the solvent boiling point (i.e. ca. 75° C.). Elevated temperature speeds up the reaction, significantly reducing its time to ca. 1.5 hours without any influence on the compound being synthesized. A preferred variant of the embodiment of invention is the use of imidazotriazinone, sulfurochloridic acid and thionyl chloride in molar ratio of 1:2.7:11. According to the embodiment of the invention the solvent, thionyl chloride, may be easily removed when the reaction is completed by vacuum distillation. In the residue containing imidazotriazinone sulfochloride, traces of thionyl chloride and water are removed by additional distillation with aprotic solvents. In the method of the present invention, the used aprotic solvents are aromatic hydrocarbons and ethers, preferably toluene and methyltetrahydrofuran or their mixtures.

Another aspect of the invention is the use of an inorganic base at the second step of synthesis of vardenafil base, i.e. imidazotriazinone sulfochloride amidation with N-ethylpiperazine. In the method of the present invention, it is preferred to use alkali metal carbonates, and the use of anhydrous sodium carbonate in solid form is particularly preferred. Anhydrous sodium carbonate as a mild alkalizing agent does not lead to the degradation of imidazotriazinone sulfochloride, however, it binds well to residues of unreacted sulfurochloridic acid, thionyl chloride, acidic products of their degradation and by-products of the reactions.

In the embodiment of the invention the imidazotriazinone sulfochloride isolated from the reaction mixture, after solvent distillation, is undergone emulgation in an aprotic solvent, preferably toluene, then anhydrous sodium carbonate is added. The resulting suspension is stirred at room temperature for 1-2 hours in order to neutralize the acidic residues of the chlorosulfonation reaction. Only then the amidation agent (N-ethylpiperazine) is added to the reaction mixture. During the amidation process the suspension of anhydrous sodium carbonates sustains anhydrous conditions and binds the by-produced hydrogen chloride. In one embodiment of the present invention, it is preferred that the amidation process is carried out under reflux at a temperature of 70-100° C., until the imidazotriazinone sulfochloride conversion is more than 99%. A preferred variant of the embodiment of the invention is to use an excess of 2.5 mole N-ethylpiperazine and 5.7 mole inorganic base for each mole of starting imidazotriazinone.

The preferred aspect of the invention is presented in Scheme 1.

Vardenafil base

In the method of the present invention, vardenafil base may be synthesized as a solution in a solvent that is later washed with water and vardenafil is extracted with aqueous hydrochloric acid as vardenafil dihydrochloride and converted in water to vardenafil sodium salt. Finally, after changing the pH to 9.0-9.5, it crystallizes as vardenafil base.

Vardenafil base synthesized according to the method of the present invention has a sufficient purity to be directly used in the production of pharmaceutically acceptable salts with acids.

The subject of the invention is also a method for the preparation of vardenafil hydrochlorides, especially vardenafil monohydrochloride trihydrate with high stability and a higher melting point (234° C.) in comparison to the vardenafil monohydrochloride trihydrate synthesized according to the methods known in the prior art. Both vardenafil monohydrochloride trihydrates are characterized by identical powder diffractograms (shown in FIG. 1 and FIG. 4 of the drawing) but have different melting points (FIG. 2 and FIG. 5).

The essence of the invention is a method for manufacturing of vardenafil monohydrochloride trihydrate with a melting point of 234° C. based on contacting a specific crystalline anhydrous form of vardenafil monohydrochloride with water in an organic solvent. According to the method of the present invention, the specific crystalline form, used to prepare vardenafil monohydrochloride trihydrate with a melting point of 234° C., is an anhydrous modification V of vardenafil monohydrochloride (anhydrous modification V).

According to the method of the present invention, the vardenafil monohydrochloride trihydrate with a high melting point is prepared by the solution of vardenafil base in an organic solvent, a preferred choice being a water-miscible organic solvent, an addition of equimolar quantity of concentrated hydrochloric acid, and then precipitation of crystalline anhydrous modification V by the partial evaporation of the solvent and/or cooling of the solvent. Water is added to the suspension of the anhydrous modification V and the mixture is stirred for several hours. The resulting vardenafil monohydrochloride trihydrate suspension is filtered, washed with organic solvent and vacuum-dried.

A preferred embodiment of the invention is the use of acetone as solvent.

Because the amount of water introduced to the process is a key parameter of the invention, vardenafil base may not contain more than 1.0% of water, and acetone may not contain more than 0.4% of water.

In a preferred variant of the embodiment of the invention, vardenafil base, with a water content of less than 1.0%, is dissolved in acetone at a temperature of 40-45° C., where the molar ratio of vardenafil base to acetone is within 1:140 and 1:150, an equimolar quantity of concentrated hydrochloric acid is added and ⅓ of the solvent is evaporated, and then the suspension of crystalline anhydrous modification V is cooled to 0-5° C. and stirred for 2 hours.

The suspension of crystalline anhydrous modification V is converted into vardenafil monohydrochloride trihydrate with a melting point of 234° C. by dropping water and stirring for several hours. In a preferred variant of the embodiment of the present invention, water is added to the acetone suspension in such a quantity so that the molar ratio of vardenafil base used to prepare the suspension of crystalline anhydrous modification V and water is within 1:5.3 and 1:6.8, followed by the suspension is contacted with water for 4-12 hours at a temperature of 0-5° C. The precipitate of vardenafil monohydrochloride trihydrate is washed with acetone and vacuum-dried at a temperature not exceeding 35° C.

A preferred aspect of the invention is presented in Scheme 2.

Vardenafil monohydrochloride trihydrate
m.p. 234° C.

Figure 3:
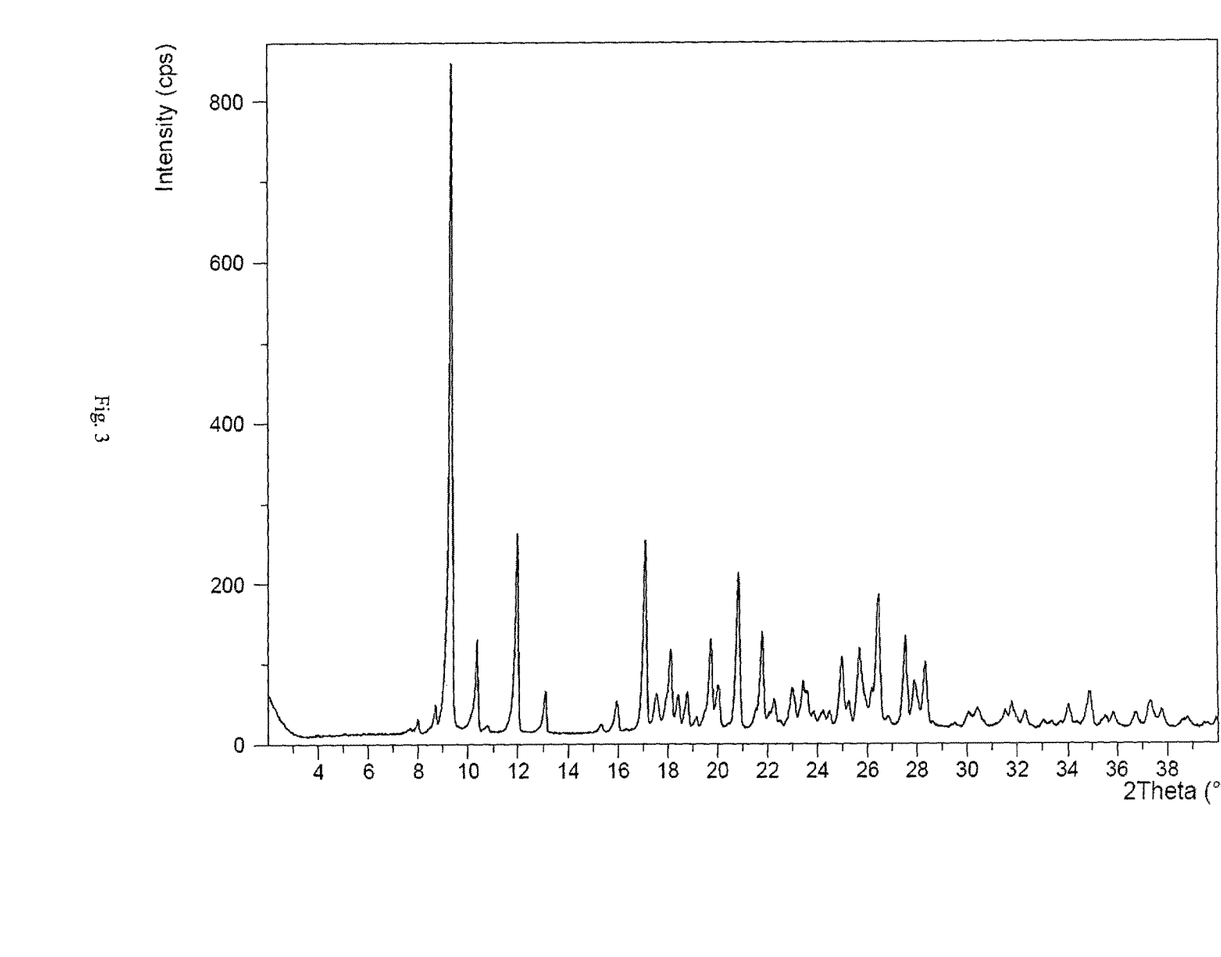
FIG. 3 presents an XRPD of anhydrous modification V of vardenafil monohydrochloride prepared in example 4.

The crystalline anhydrous modification V of monohydrochloride is characterized by X-ray Powder Diffraction pattern presented in FIG. 3 and a melting point of 234° C. The anhydrous vardenafil monohydrochloride crystalline modification V in crystalline form is characterized by the following set of peak positions in powder diffractogram, described by interplanar distances d (Å) and diffraction angles 2Θ(°) of X-rays of Cu K-Alpha (1.5418740 Å):

| d(Å) | 2Θ (°) |
| --- | --- |
| 9.444 | 9.37 |
| 8.527 | 10.37 |
| 7.386 | 11.98 |
| 6.756 | 13.11 |
| 5.554 | 15.96 |
| 5.185 | 17.10 |
| 4.895 | 18.12 |
| 4.498 | 19.74 |
| 4.263 | 20.84 |
| 4.079 | 21.79 |
| 3.367 | 26.45 |
| 3.237 | 27.54 |
| 3.148 | 28.61 |

In the embodiment of the invention, the anhydrous modification V is obtained by the dissolution of vardenafil base in an water-miscible organic solvent, preferably acetone, followed by an addition of equimolar quantity of concentrated hydrochloric acid. The crystallization of the anhydrous modification V is forced by the increase a concentration of the solution and/or by decreasing its temperature. The suspension is filtered, washed with organic solvent and vacuum-dried at a temperature of 30-35° C.

The crystalline anhydrous modification V of vardenafil monohydrochloride is a useful intermediate for the synthesis of vardenafil monohydrochloride trihydrate with a melting point of 234° C.

In one of the embodiment of the present invention, it is possible to prepare the vardenafil monohydrochloride trihydrate with a melting point of 234° C. by suspension of the crystalline anhydrous modification V of vardenafil monohydrochloride containing less than 1% of water in a water-miscible organic solvent, addition of water and stirring for several hours.

In a preferred embodiment of the invention, the anhydrous modification V is suspended in acetone, where the molar ratio of anhydrous modification V to acetone is between 1:90 and 1:100, then water is added, where a preferred molar ratio of anhydrous modification V to water is 1:5.3 to 1:6.8 and stirred for 4-12 hours at a temperature of 0-5° C. The precipitate of vardenafil monohydrochloride trihydrate is washed with acetone and vacuum-dried at a temperature of 30-35° C.

The method of the present invention enables an effective synthesis of vardenafil base with a 20-35% increase in yield as compared to methods known in the prior art. The effectiveness was significantly increased by shorter reaction times resulting from a carrying out of the reaction under reflux. In the key step of vardenafil base synthesis it was possible to reduce the chlorinating agent, sulfurochloridic acid, to nearly stoichiometric quantities. The chlorinating solvent used at this step of synthesis may be easily removed from the reaction environment by distillation and reused.

An important aspect of the invention is the elimination of aqueous wastes which are produced in considerable amounts in the step of the isolation of imidazotriazinone sulfonic acid or imidazotriazinone sulfochloride, as per methods known in the prior art.

The requirements established by the International Conference on Harmonization (ICH) with regard to pharmaceutical substances for human use enforce a search for new and more effective methods for the reduction of impurities in active substances. The process of the present invention fulfills these requirements because it enables a synthesis of vardenafil base with the content of the active substance over 99.7% and the content of any particular impurity below 0.10%. Vardenafil base of such purity is suitable for direct use in the production of pharmaceutically acceptable salt with acid without additional purification.

According to the method of the present invention, from such a pure vardenafil base, one may synthesize vardenafil monohydrochloride trihydrate with precisely defined physical parameters by the use of a new anhydrous modification V of the vardenafil monohydrochloride. The strict compliance with the regime of process, according to the method of present invention, allows for obtaining the vardenafil monohydrochloride trihydrate characterized by a melting point of 234° C. as a pure product without an admixture of any other polymorphic forms.

ANALYTICAL METHODS

The purity of the prepared vardenafil base was determined by UHPLC, performed by a liquid chromatograph capable of ultra-high performance liquid chromatography. The column was filled with C18 with grain size of 1.8 μm and gradient elution.

X-ray Powder Diffraction patterns were performed with a PANalytical X'Pert PRO MPD with Bragg-Brentano geometry equipped with a Cu anode lamp and a RTMS X'Celerator detector.

DSC analysis was performed with a Mettler Toledo DSC822$^e$ with a temperature range of 30-270° C., heating rate of 10° C./min and nitrogen atmosphere with a flow of 80 ml/min.

EXAMPLES

Example 1

Synthesis of vardenafil base (2-[2-ethoxy-5-(4-ethylpiperazine-1-sulfonyl)-phenyl]-5-methyl-7-propyl-3H-imidazo[5,1-f][1,2,4]triazin-4-one)

To a 0.1 dm$^3$ round-bottom flask equipped with a mechanical stirrer and a thermometer the following were added: 40 ml (0.554 mol) of thionyl chloride, 15.65 (0.05 mol) of imidazotriazinone, then for 5 minutes 9 ml (0.135 mol) of sulfurochloridic acid was dropped in. The mixture was heated to boiling point and kept at that condition for 1.5 hours. After the completion of the chlorosulfonation reaction, the mixture was cooled to ca. 50° C. and excess thionyl chloride was vacuum-distilled. To the residue, 20 ml of toluene was added twice and the solvent was vacuum-distilled. The residue, containing imidazotriazinone sulfochloride, was emulgated in 500 ml of toluene and transferred to a 1.0 dm$^3$ flask equipped with a mechanical stirrer and a thermometer, after that 30 g (0.283 mol) of anhydrous sodium carbonate was added. The suspension was stirred in ca. 20° C. for 1 hour, then 15.86 ml (0.125 mol) of N-ethylpiperazine was dropped in at room temperature. The mixture was heated to boiling point and stirred under these conditions for 2 hours until the conversion of imidazotriazinone sulfochloride was over 99% (HPLC). The obtained product was a vardenafil free base dissolved in toluene.

Example 2

Isolation of Vardenafil Free Base (2-[2-ethoxy-5-(4-ethylpiperazine-1-sulfonyl)-phenyl]-5-methyl-7-propyl-3H-imidazo[5,1-f][1,2,4]triazin-4-one)

To a hot reaction mixture obtained in example 1, 400 ml of water was added and the resulting mixture was cooled to ca. 70° C. The stirring was continued for 15 minutes, after that the organic and aqueous phases were separated. The aqueous phase was removed into the liquid wastes. The organic phase extraction with 200 ml of water was repeated in ca. 60° C. Then the organic phase was added to 300 ml of water in a 1.5 dm$^3$ flask equipped with a mechanical stirrer, a thermometer and a pH-meter. A 17% aqueous hydrochloric acid was dropped in accompanied by vigorous stirring until pH was adjusted in the range of 1.5-2.0. The stirring was continued for 15 minutes, after which phases were separated. The toluene phase was transferred for regeneration and to the aqueous phase containing vardenafil dihydrochloride was added 1000 ml of water and it was heated to the temperature of ca. 90° C. Then to a hot aqueous solution of vardenafil dihydrochloride (2-[2-ethoxy-5-(4-ethylpiperazine-1-sulfonyl)-phenyl]-5-methyl-7-propyl-3H-imidazo [5,1-f][1,2,4]-triazin-4-one) dihydrochloride), 15% aqueous solution of NaOH was dropped in until pH was adjusted in the range of 10.5-11.0. The mixture was stirred at ca. 90° C. until the solution was clear, after that 17% aqueous solution of hydrochloric acid was dropped to adjust pH in the range of 9.0-9.5 and vardenafil base was precipitated. The suspension was cooled to room temperature, pH corrected to 9.0-9.5 with hydrochloric acid and the mixture stirred for 1 hour at ca. 20° C. and then filtered. The suspension was washed with 300 ml of water at ca. 20° C. and dried at 70° C.

23.5 g of vardenafil base was obtained with a 96% yield calculated on the starting imidazotriazinone.

HPLC confirmed content of active substance over 99.7%, while each individual impurity did not exceed 0.10%. Water content was 0.8%.

Example 3(Reference Example)

Preparation of vardenafil monohydrochloride trihydrate (2-[2-ethoxy-5-(4-ethylpiperazine-1-sulfonyl)-phenyl]-5-methyl-7-propyl-3H-imidazo[5,1-f][1,2,4]triazin-4-one)monohydrochloride trihydrate) having a low melting point.

To a 0.5 dm³ flask equipped with a mechanical stirrer, a thermometer and a pH-meter 300 ml water was added and suspended 20 g (0.04 mol calculated on a dry matter) vardenafil base, wet or dried, as obtained in example 2. An 18% aqueous hydrochloric acid was dropped in until pH was adjusted in the range of 1.5-2.0. Then 15 g of activated carbon was added and the mixture was stirred for 1 hour at ca. 30° C., after which carbon was filtered out and, to the remaining mixture 10% aqueous NaOH was dropped in until pH was adjusted in the range of 3.8-4.5. The mixture was heated to ca. 45° C. and stirred at this temperature for 0.5 hour. Aqueous solution of vardenafil monohydrochloride was crystallized by cooling of the solution to 10° C., after which stirring was continued for 2 hours. The vardenafil monohydrochloride trihydrate precipitate was filtered and washed with 40 ml of demineralized water. The product was dried up in a vacuum drier at a temperature of ca. 30° C. for 12 hours. 23.2 g (ca. 80% yield) of vardenafil monohydrochloride trihydrate having a melting point of 202° C. was prepared.

Figure 1:
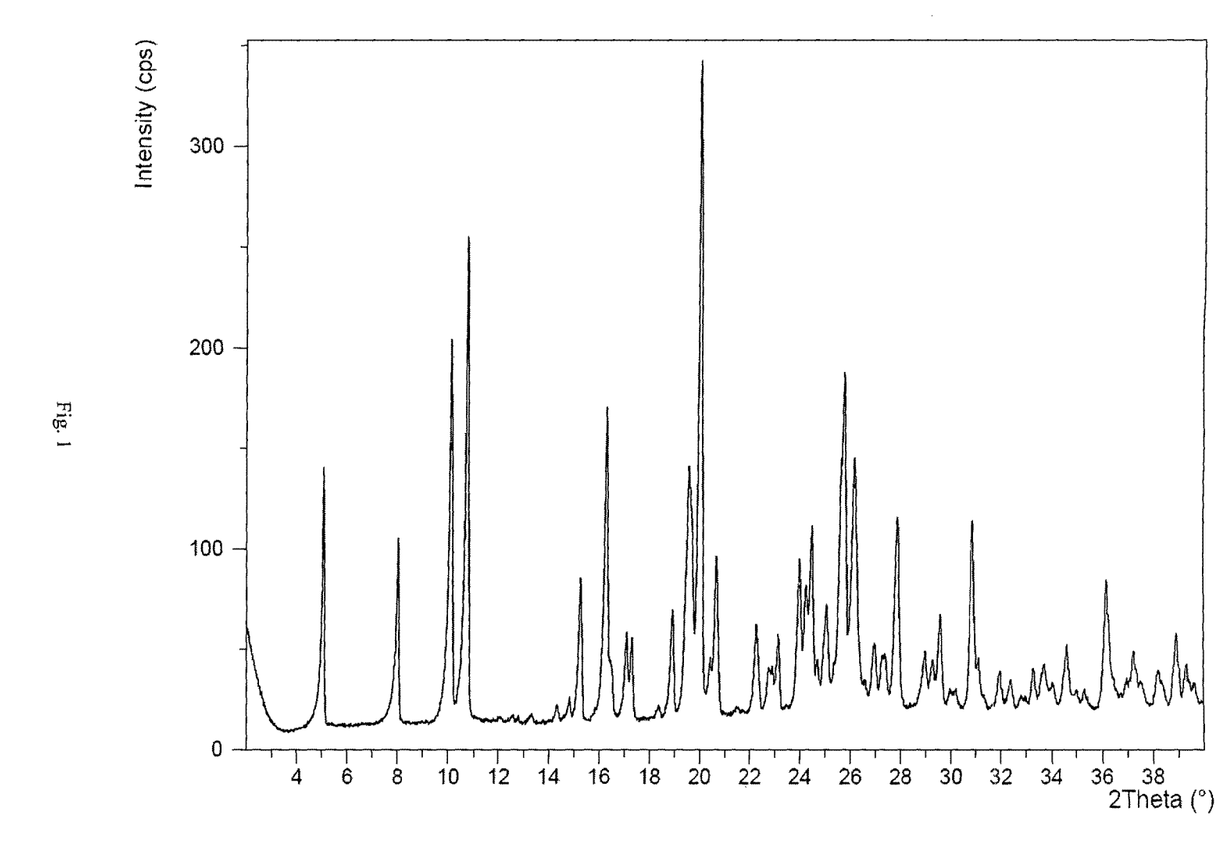
FIG. 1 presents an XRPD of vardenafil monohydrochloride trihydrate prepared in example 3
Figure 2:
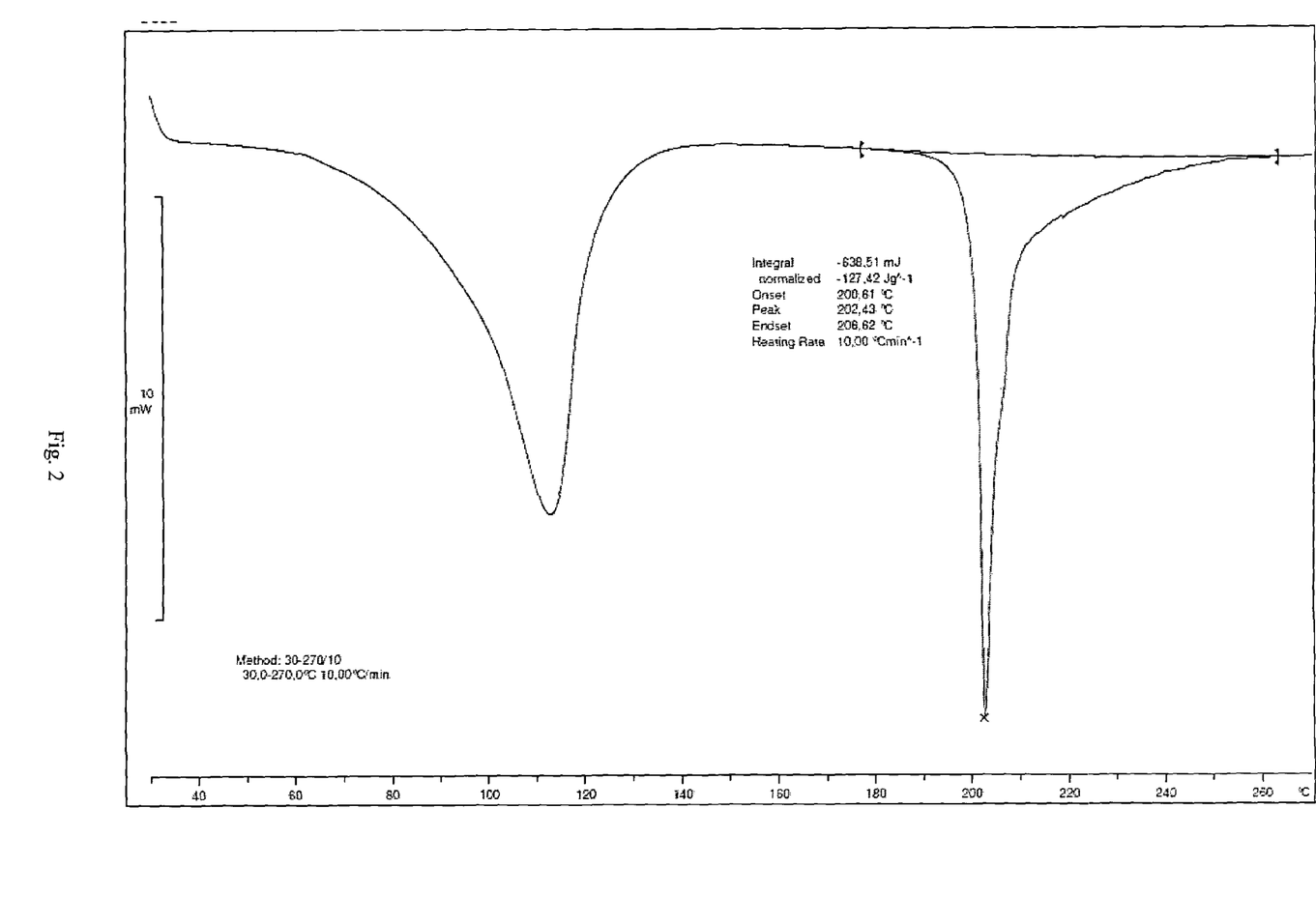
FIG. 2 presents a DSC of vardenafil monohydrochloride trihydrate prepared in example 3

X-ray Powder Diffraction and DSC of the compound is shown in FIG. 1 and FIG. 2.

Example 4

Preparation of vardenafil monohydrochloride trihydrate (2-[2-ethoxy-5-(4-ethylpiperazine-1-sulfonyl)-phenyl]-5-methyl-7-propyl-3H-imidazo[5,1-f][1,2,4]triazin-4-one)monohydrochloride trihydrate) Having a Melting Point of 234° C.

To a 0.5 dm³ flask equipped with a mechanical stirrer and a thermometer 420 ml acetone was poured in (water content below 0.4% KF) and 20.0 g (0.04 mol) of dried vardenafil base (water content below 1.0% KF) as obtained in example 2 was suspended. The suspension was heated to ca. 45° C. and stirred until dissolution occurred. Then, to the clear solution, a stoichiometric quantity (3.78 ml, 0.04 mol) of concentrated hydrochloric acid (36%) was dropped in. The solution was stirred at ca. 40° C. for 2 hours, after which 140 ml of acetone was distilled and the mixture was cooled to ca. 0 C. The stirring of the suspension of the anhydrous modification V was continued at ca. 0° C. for 2 hours, after that 4.0 ml water was dropped in. The suspension was contacted with water, by being stirred at 0° C. for at least 4 hours. The suspension was filtered and washed by 20 ml acetone, then vacuum-dried at ca. 30° C. for 4 hours.

16.6 g (70% yield) of vardenafil monohydrochloride trihydrate having a melting point of 234° C. was prepared.

X-ray Powder Diffraction pattern of the anhydrous modification V of vardenafil monohydrochloride is shown in FIG. 3.

Figure 4:
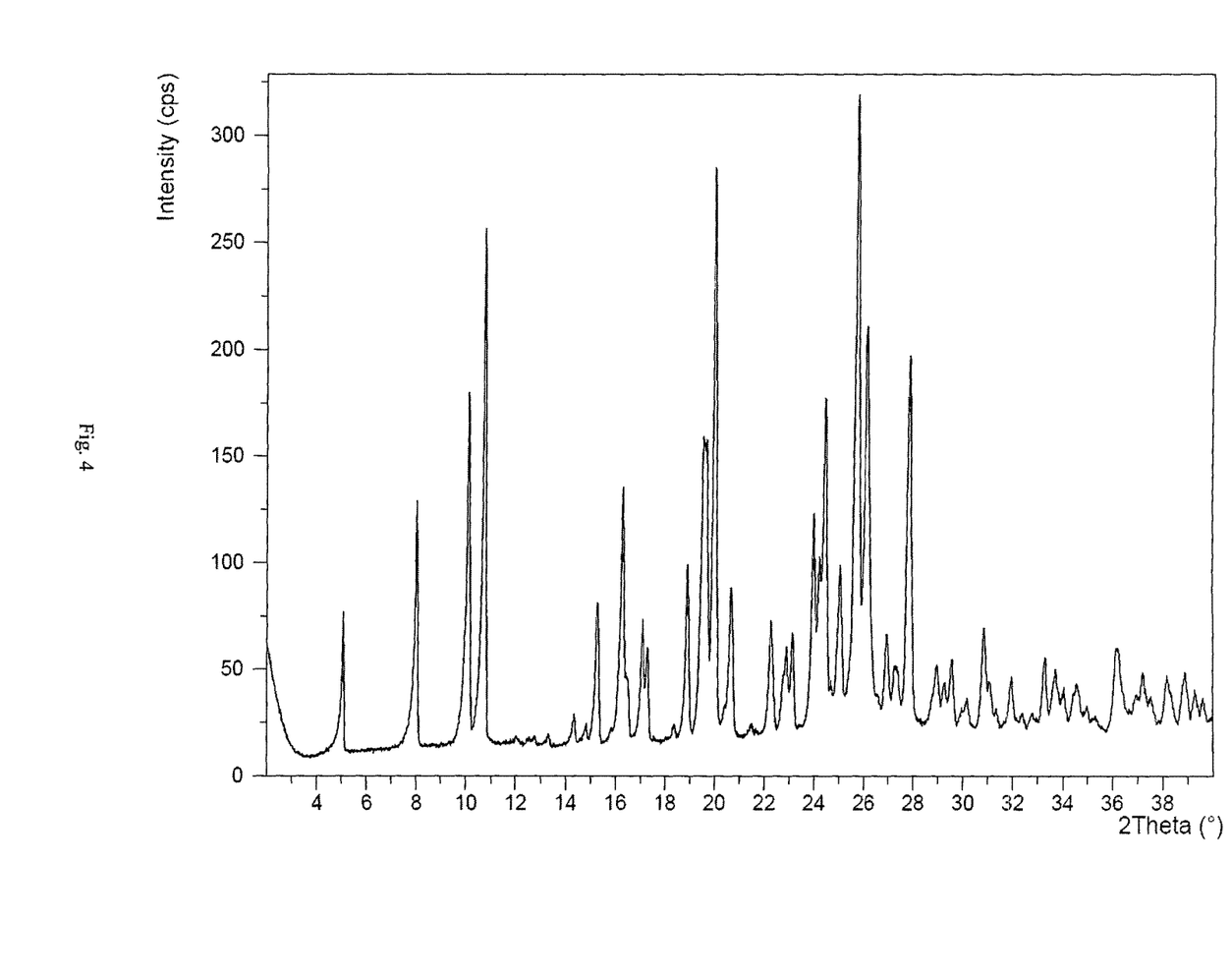
FIG. 4 presents an XRPD of vardenafil monohydrochloride trihydrate prepared in example 4
Figure 5:
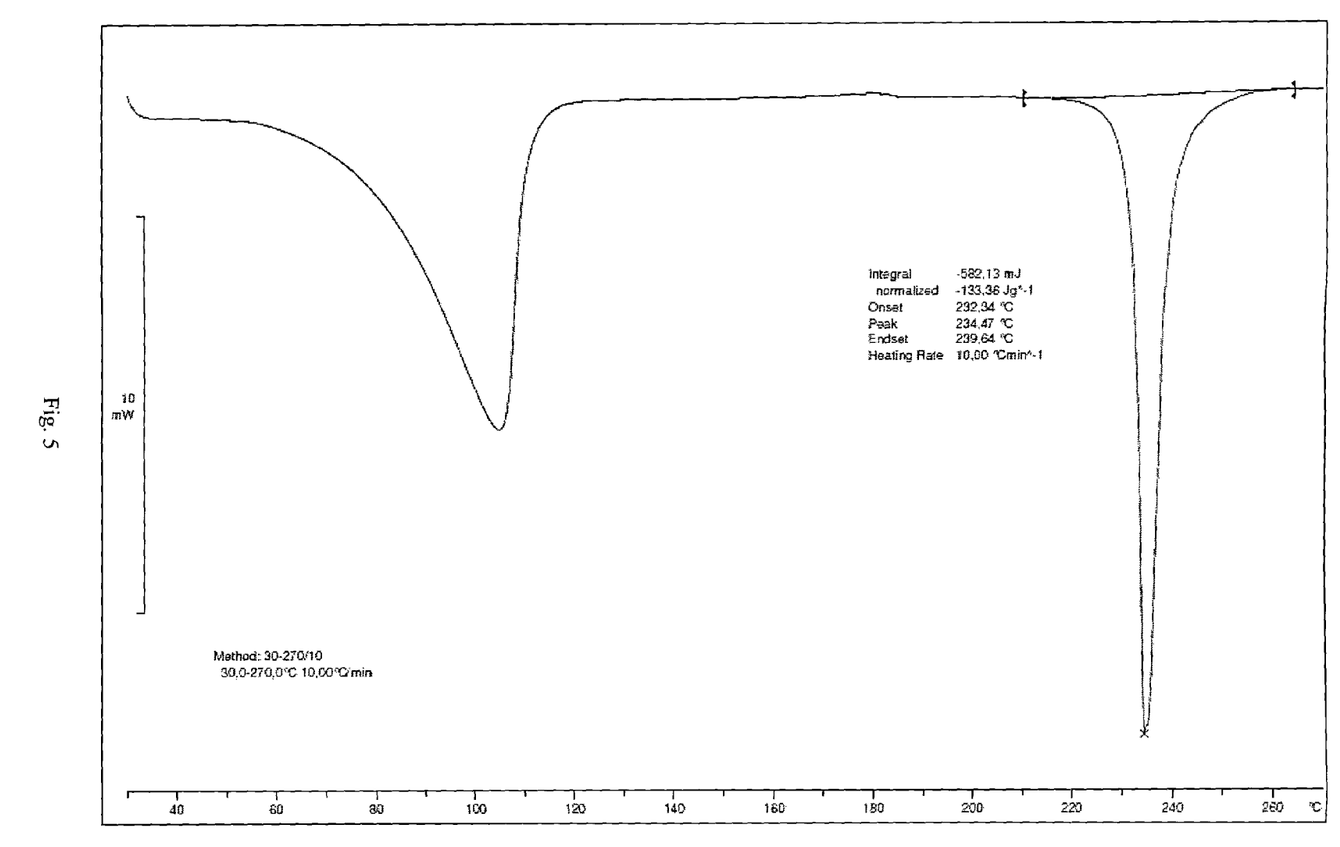
FIG. 5 presents a DSC of vardenafil monohydrochloride trihydrate prepared in example 4

X-ray Powder Diffraction pattern and DSC of the prepared vardenafil monohydrochloride trihydrate is shown in FIG. 4 and FIG. 5.

The invention claimed is:

1. A method for manufacturing vardenafil and/or its salts, comprising chlorosulfonating 2-(2-ethoxy-phenyl)-5-methyl-7-propyl-3H-imidazo[5,1-f][1,2,4]triazin-4-one in thionyl chloride mixed with sulfurochloridic acid under reflux at the solvent boiling point, isolating the synthesized 4-ethoxy-3-(5-methyl-4-oxo-7-propyl-3,4-dihydroimidazo[5,1-f][1,2,4]triazin-2-yl)benzene-sulfonic acid chloride from the reaction mixture under anhydrous conditions, amidating the 4-ethoxy-3-(5-methyl-4-oxo-7-propyl-3,4-dihydroimidazo[5,1-f][1,2,4]triazin-2-yl)benzene-sulfonic acid chloride with N-ethylpiperazine in an aprotic solvent in the presence of an inorganic base, and after completion of the reaction, isolating the prepared vardenafil base and optionally transforming the vardenafil base into a salt.

2. The method for manufacturing vardenafil of claim 1, wherein the molar ratio of 2-(2-ethoxy-phenyl)-5-methyl-7-propyl-3H-imidazo[5,1-f][1,2,4]triazin-4-one to sulfurochloridic acid and thionyl chloride is 1:2.7:11.

3. The method for manufacturing vardenafil of claim 1, wherein the inorganic base is anhydrous sodium carbonate.

4. The method for manufacturing vardenafil of claim 1, wherein the aprotic solvent is toluene.

5. The method for manufacturing vardenafil of claim 1, wherein the ratio of N-ethylpiperazine and inorganic base in relation to the 2 (2 ethoxy-phenyl)-5-methyl-7-propyl-3H-imidazo[5,1-f][1,2,4]triazin-4-one is 1:2.5:5.7.

6. The method for manufacturing vardenafil of claim 1, wherein the amidation reaction are carried out under reflux.

7. The method for manufacturing vardenafil of claim 1, wherein the vardenafil salt is vardenafil hydrochloride.

8. The method for manufacturing vardenafil of claim 1, wherein the vardenafil salt is vardenafil monohydrochloride trihydrate.

9. A method for manufacturing vardenafil monohydrochloride trihydrate having a melting point of 234° C. comprising:
   a. dissolving vardenafil base in an organic solvent;
   b. adding a stoichiometric quantity of concentrated hydrochloric acid;
   c. precipitating anhydrous modification V of vardenafil monohydrochloride;
   d. contacting a suspension of the anhydrous modification V of vardenafil monohydrochloride with water,
   e. filtering, washing and drying the suspension of vardenafil monohydrochloride trihydrate to provide the vardenafil monohydrochloride trihydrate having a melting point of 234° C.,
   wherein anhydrous modification V of vardenafil monahydrochloride is characterized on powder diffractogram by the following set of peak positions, described by interplanar distances d (Å) and diffraction angles 2Θ(°):

| d(Å) | 2Θ (°) |
| --- | --- |
| 9.444 | 9.37 |
| 8.527 | 10.37 |
| 7.386 | 11.98 |
| 6.756 | 13.11 |
| 5.554 | 15.96 |
| 5.185 | 17.10 |
| 4.895 | 18.12 |
| 4.498 | 19.74 |
| 4.263 | 20.84 |
| 4.079 | 21.79 |
| 3.367 | 26.45 |
| 3.237 | 27.54 |
| 3.148 | 28.61. |

10. The method of claim 9, wherein the vardenafil base contains less than 1.0% of water.

11. The method of claim 9, wherein the organic solvent is a water-miscible solvent with a water content of less than 0.4%.

12. The method of claim 11, wherein the water-miscible organic solvent is acetone.

13. The method of claim 9, wherein the molar ratio of vardenafil monohydrochloride to added water is 1:5.55 and the contacting time of anhydrous modification V of vardenafil monohydrochloride and water is at least 4 hours.

14. The method of claim 9, wherein the vardenafil monohydrochloride trihydrate is vacuum-dried at 30-35° C.

15. An anhydrous modification V of vardenafil monohydrochloride in crystalline form characterized on powder diffractogram by the following set of peak positions, described by interplanar distances d (Å) and diffraction angles 2Θ(°):

| d(Å) | 2Θ (°) |
| --- | --- |
| 9.444 | 9.37 |
| 8.527 | 10.37 |
| 7.386 | 11.98 |
| 6.756 | 13.11 |
| 5.554 | 15.96 |
| 5.185 | 17.10 |
| 4.895 | 18.12 |
| 4.498 | 19.74 |
| 4.263 | 20.84 |
| 4.079 | 21.79 |
| 3.367 | 26.45 |
| 3.237 | 27.54 |
| 3.148 | 28.61. |

16. The anhydrous modification V of vardenafil monohydrochloride in crystalline form of claim 15, wherein its melting point is 234° C.

* * * * *